United States Patent [19]

Nakatomi et al.

[11] Patent Number: 4,693,898

[45] Date of Patent: Sep. 15, 1987

[54] NOVEL BAKER'S YEAST AND PROCESS FOR MAKING BREAD

[75] Inventors: Yasuo Nakatomi, Chiba; Katsuhiko Hara; Fumio Umeda, both of Saitama; Toshiaki Kono, Kanagawa; Hisashi Niimoto, Tokyo, all of Japan

[73] Assignees: Oriental Yeast Co., Ltd.; Meiji Seika Kaisha, Ltd., both of Tokyo, Japan

[21] Appl. No.: 848,854

[22] Filed: Apr. 4, 1986

[30] Foreign Application Priority Data

Apr. 9, 1985 [JP] Japan .................................. 60-73580

[51] Int. Cl.$^4$ .......................... C12N 1/18; A21D 2/00
[52] U.S. Cl. ........................................ 426/19; 426/62; 435/256
[58] Field of Search ...................... 435/256; 426/62, 19

[56] References Cited

U.S. PATENT DOCUMENTS 4,431,737 2/1984 Olivieri et al. ................... 435/256 X
4,450,238 5/1984 Vitobello et al. .................... 435/256

OTHER PUBLICATIONS

Chemical Abstracts, vol. 95, No. 21 (1981), 183746b.

*Primary Examiner*—Joseph Golian
*Attorney, Agent, or Firm*—Browdy and Neimark

[57] ABSTRACT

This invention relates to a novel baker's yeast having sucrose-nonfermentability and suitability for making bread. Further, this invention relates to a process for making bread containing fructooligosaccharide, using said yeast.

6 Claims, No Drawings

NOVEL BAKER'S YEAST AND PROCESS FOR MAKING BREAD

This invention relates to a novel baker's yeast used for making bread containing fructooligosaccharides and a process for making bread, using said novel baker's yeast.

In general, fructooligosaccharide is a compound in which 1 to 3 or more molecules of fructose is $\beta$-combined to fructose of sucrose at the position of $C_1$ and $C_2$, and its chemical structure is as follows:

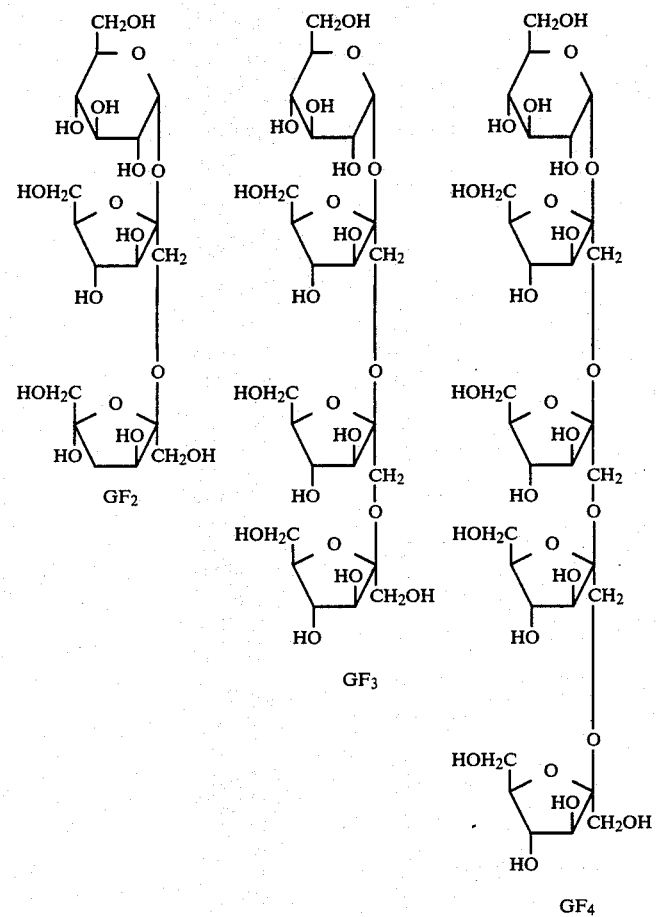

GF$_2$: 1-Kestose
GF$_3$: Nystose
GF$_4$: 1$^F$-Fructofuranosyl nystose

These fructooligosaccharides are widely distributed among higher plants, for example, asparagus, onion, Jerusalem artichoke, honey and the like. Recently methods for mass production of fructooligosaccharide from sucrose by means of microbial enzymes were established, so physical and physiological properties of these fructooligosaccharides were widely examined. It was found that the fructooligosaccharide is a nondigestive sugar and has excellent physiological effects such as selective growth factor of Bifidobacteria in the intestine, improving effect on serum lipid metabolism, and low cariogenicity. Furthermore, fructooligosaccharides taste like sugar, so the usefullness of fructooligosaccharides as new materials in the field of food has become apparent.

To produce such excellent physiological effects, said fructooligosaccharide is preferably ingested day after day. For that purpose, the fructooligosaccharide is appropriate to be mixed in a food which is habitually ingested everyday in diet, and the amount is considered as approximately 5 g per day.

Among the typical foods suited for such conditions is bread. Although bread generally contains a large amount of sucrose in its dough, fructooligosaccharide can be used in place of all or a portion of this sucrose.

However, as the baker's yeasts presently used for making bread are sucrose-fermentable and have invertase activity, there is a problem in which the fructooligosaccharide added on purpose is decomposed by the invertase in vain.

Then, though sucrose-nonfermentable type strains belonging to Saccharomyces cerevisiae such as Lina, Linα, and Lina×Linα were tried to be used for making bread, their dough-leavening activity was weak and, thus, they were proved to be yeasts possibly unusable for making bread. As to the sucrose-nonfermentable Saccharomyces yeasts, there are some descriptions about the type strains used for genetic research or classification so far, but those put to practical use as baker's yeast have not been known.

This invention came to a consideration that if the excellent property of the sucrose-fermentable baker's yeast having suitability for making bread of the same Saccharomyces cerevisiae can be given to a sucrose-nonfermentable yeast, a yeast having sucrose-nonfermentability and suitability for making bread can be obtained.

As a result of earnest studies based on this consideration, the present inventors have succeeded in breeding of a baker's yeast meeting to this purpose.

This invention relates to a baker's yeast having sucrose-nonfermentability and suitability for making bread and utilization thereof.

To give the suitability for making bread to sucrose-nonfermentable laboratory strains having no suitability for making bread, these strains are crossed with a baker's yeast having suitability for making bread by means of mating or cell fusion, to make hybrid strains, and by the formation and isolation of their spores, spore cultures are obtained, among which those having sucrose-nonfermentability are selected. Further, repeating crossing, spore isolation and selection between the sucrose-nonfermentable spore cultures and the baker's yeast, as the occasion demands, sucrose-nonfermentable spore cultures having genetic factors of excellent suitability for making bread are obtained. By crossing among the spore cultures thus obtained, hybrid strains having sucrose-nonfermentability and suitability of making bread can be created. As an embodiment of the present invention, FIG. 1-IL-1, FERM, P-8056 is illustrated as reference.

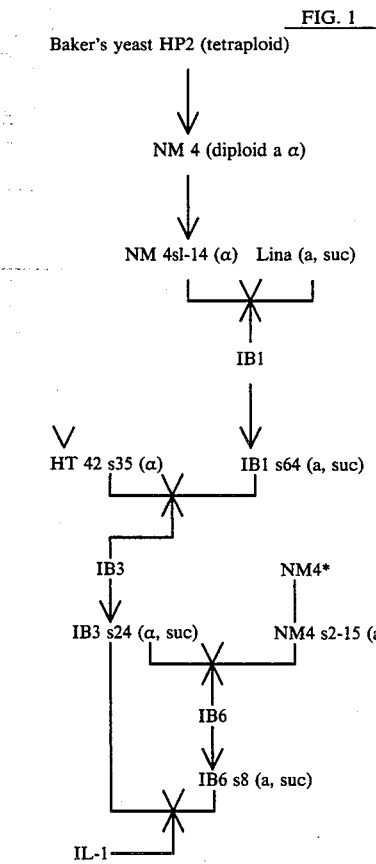

FIG. 1

Spore culture NM 4s1-14 (sucrose-fermentable) isolated from NM4 (diploid a α), Spore culture of a baker's yeast HP2 (commercially available Oriental yeast, tetraploid), was crossed to breed IB1. By formation of IB1 spores and isolation thereof, a large number of spore cultures were obtained, among which sucrose-nonfermentable IB1 s64 was selected. This was in turn crossed with HT 42s35 derived from the baker's yeast (commercially available Oriental yeast) to breed IB3. A large number of spore cultures were obtained by formation of IB3 spore and isolation thereof, among which sucrose-nonfermentable IB3 s24 was selected and crossed with a spore culture from NM4, NM4 s2-15, to breed IB6. By formation of IB6 spores and isolation thereof, a large number of spore cultures were obtained, among which sucrose-nonfermentable IB6 s8 was selected and crossed with the above-said IB3 s24 to breed a hybrid strain. This strain is sucrose-nonfermentable Saccharomyces cerevisiae*, named IL-1 according to classification by The Yeasts, A Taxonomic Study, Third revised and enlarged edition, Edited by N. J. Kr-ger-van-Rij, and deposited as FERM P-8056 in Fermentation Research Institute.

Mycological properties of Saccharomyces cerevisiae IL-1

1. Growth conditions
   Excellent growth in MY liquid medium
   Shape of cell: Globular-oval, $3-7 \times 4-8\mu$
   Growth of YM agar medium Excellent growth, Colony (white, grossy, smooth)
2. Ascospore
   Formed on potassium acetate agar medium
   Shape of ascospore: globular
3. Physiological properties
   (1) Optimum growth conditions:
       Temp. 28°–32° C.,
       pH 4.5–6.5
   (2) Range of growth:
       Temp. 0°–40° C.,
       pH 2.5–8.0
   (3) No assimilation of nitrates
   (4) No decomposition of fat
   (5) No formation of carotenoids
   (6) No remarkable formation of organic acids
   (7) Vitamin requirement: Biotin and pantothenic acid are required.
4. Fermentation and assimilation of carbon compounds

|  | Fermentation | Assimilation |
|---|---|---|
| D-glucose | + | + |
| D-galactose | + | + |
| Maltose | + | + |
| Sucrose | − | − |
| 1-Kestose (GF2) | − | − |
| Nystose (GF3) | − | − |
| Lactose | − | − |
| Raffinose | − | − |
| Melibiose | − | − |
| Trehalose | − | − |
| Melezitose | − | − |
| α-Methyl-D glucoside | − | − |
| Dextrin | + | + |
| Cellobiose | − | − |
| D-ribose | − | − |
| D-xylose | − | − |
| L-arabinose | − | − |
| Ethanol |  | + |
| DL-lactate |  | + |
| Glycerin |  | + |

The use of Saccharomyces cerevisiae IL-1 in this invention enables the fructooligosaccharide added to starting materials for bread to almost remain without decomposition and can afford excellent spongy bread. Breads to be made in this invention include a loaf of bread, bun, cracker, hardtack and the like.

This invention is further illustrated by the following examples.

EXAMPLE 1

Using *Saccharomyces cerevisiea* IL-1, the incubation was carried out according to the following method by means of a 30L Jar Fermenter.

Seed culture No. 1
  Medium: YPG medium
    Glucose 2%
    Peptone 2%
    Yeast extract 1%
  Culture conditions, 30° C., shaking, 24 hr
  Medium amount 5 ml
Seed culture No. 2
  Medium: YPG medium
  Culture conditions: shaking 30° C., 40 hr
  medium amount 100 ml
Preliminary culture
  Inoculating amount 100 g
  Amount of Molasses used 3.0 l (sugar 30%)
  Chemical additives
    Urea as nitrogen against sugar 5.0%
    Sodium dihydrogenphosphate as phosphorus against sugar 0.5%
  Culture conditions 30° C.
    Aeration, 3.0 l/min; Stirring, 400 rpm;
    Fed-batch culture, 16 hr
Main culture
  Inoculating amount 250 g
  Used amount of Molasses, 3.5 l (sugar 30%)
  Chemical additives
    Urea as nitrogen against sugar 3.5%
    Sodium dihydrogenphosphate as phosphorus against sugar 0.35%
  Culture conditions, 30° C.
    aeration, 30 l/min; Stirring, 400 rpm,
    Fed-batch culture, 14 hr
  Medium amount
    Initial 12 l, Final 16 l After cultivation, the cells were harvested, washed with water, and dehydrated to make a compressed yeast. The Molasses used here is those in which sucrose is inversed by invertase.

The *Saccharomyces cerevisiae* IL-1 obtained in the above incubation was tested for liquid fermentation and bread-making ability.

The liquid fermentation force test is carried out with the Modified Wolf's fermenter (Baker's Yeast Test of the Japan Yeast Industry Association). Each medium is based on the medium by Schultz et al., and adjusted to the following sugar concentration.

F SG(40): 8 g of Sucrose and 1 g of glucose are dissolved in water to make the volume 20 ml.

F G(5): 1 g of Glucose is dissolved in water to make the volume 20 ml.

F f(10): 2 g of Fructooligosaccharide (purity 95%)

The liquid fermentation ability is indicated by $CO_2$ gas produced at 30° C. for 2 hours (after addition of 5 ml of the yeast suspension containing 150 mg (dry matter) to 15 ml of medium).

$$(\text{Storage stability}) = \frac{F(40) \text{ after storage at 30° C. for 3 days}}{F(40) \text{ just after culture}} \times 100\% \quad S(40)$$

Medium by Schultz et al.: Shultz, A.S., Atkin, L., Frey, C.N. Cereal, Chem., 22, 321 (1945).

The test results are summarized in Table 1. The baking test is carried out according to the following conditions.

| (Formula) | |
|---|---|
| Bread flour | 100 (weight parts) |
| Salt | 2 |
| Invert sugar | 2 |
| Shortening | 6 |
| Non fat dry milk | 2 |
| Fructooligosaccharide syrup | 6 |
| (Solid part 75%) | |
| (Fructooligosaccharide 57%, sucrose 8%, glucose 33%, fruit sugar 2%) | |
| Dough improver | 0.2 |
| Water | 62 |
| Yeast | 4 |

(Process)

Mixing time: Low speed 1 min, Mid speed 6 min, High speed 2 min
Mixing up temp.: 22° C.
Fermentation time: 90 min
Divided dough weight: 360 g
Proofing time: Till the dough is raised up to 2 cm above the pan
Baking: 200°–210° C., 20 min The test results are shown in Table 1.

TABLE 1

| Item | | Kind | |
|---|---|---|---|
| | | IL-1 | Commercial yeast |
| Liquid fermentation | (ml) | | |
| | F SG(40) | 85 | 56 |
| | F G(10) | 162 | 170 |
| | F f(10) | 10 | 160 |
| Bread | (hr:min) | | |
| | 1st Fermentation time | 1:35 | 1:20 |
| | Proofing time | 45 | 40 |
| | Total required time | 3:45 | 3:25 |
| | Loaf volume (ml) | 1830 | 2020 |

As apparent from Table 1, the bread obtained after Baking Test is as excellent as the control. As a result of analysis of fructooligosaccharide, using a high performance liqid chromatography, the residual rate of fructooligosaccharides in the bread using *Saccharomyces cerevisiae* IL-1 was 96%.

On the other hand, in the bread using the commercially available baker's yeast, the fructooligosaccharide hardly remained.

WORKING EXAMPLE 2

Using *Saccharomyces cerevisiae* IL-1, FERM P-8056 culture in Example 1, a bun was made according to the conditions described below.

| (Formula) | |
|---|---|
| Bread flour | 100 |
| Salt | 0.8 |
| Invert sugar | 22 |

-continued

| (Formula) | |
|---|---|
| Shortening | 8 |
| Non fat dry milk | 2 |
| Fructooligosaccharide | 6 |
| Dough improver | 0.2 |
| Water | 55 |
| Yeast | 6 |

(Process)

Mixing time: Low speed 1 min, Mid speed 6 min, High speed 2 min
Mixing up temp.: 24° C.
Fermentation time: 90 min
Divided dough weight: 360 g
Proofing time: Till the dough is raised up to 2 cm above the pan.
Baking: 200°–210° C., 20 min As a result of analysis of the obtained bun as above, the residual rate of the fructooligosaccharide was 94%.

What is claimed is:

1. A process for making bread, which comprises the steps of mixing flour, water, fructooligosaccharide, a strain of yeast called *Saccharomyces cerevisiae* IL-1, FERM P-8056 and a hexose fermentable by said yeast strain, in proportions effective for making bread; leavening said mixture; then baking said leavened mixture to thereby obtain bread in which the fructooligosaccharide has not been decomposed.

2. A process for making bread according to claim 1, wherein the hexose is glucose.

3. In a process for the production of bread comprising the steps of mixing bread making ingredients including a fructooligosaccharide and a hexose, leavening said mixture of bread making ingredients and then baking said leavened mixture, the improvement wherein said leavening is performed by the fermentative action of *Saccharomyces cerevisiae* IL-1, FERM P-8056 upon said hexose.

4. A mixture comprising flour, water, fructooligosaccharide, a strain of yeast called *Saccharomyces cerevisiae* IL-1, FERM P-8056 and a hexose fermentable by said yeast strain, in proportions effective for making bread.

5. In a mixture of bread making ingredients comprising flour, water, fructooligosaccharide, yeast and a hexose fermentable by said yeast, the improvement wherein said yeast comprises *Saccharomyces cerevisiae* IL-1, FERM P-8056.

6. An essentially pure culture of *Saccharomyces cerevisiae* IL-1, FERM P-8056.

* * * * *